United States Patent
Sliski et al.

(10) Patent No.: US 6,302,581 B1
(45) Date of Patent: Oct. 16, 2001

(54) SUPPORT SYSTEM FOR A RADIATION TREATMENT APPARATUS

(75) Inventors: Alan P. Sliski, Lincoln; Kenneth J. Harte, Carlisle, both of MA (US)

(73) Assignee: Photoelectron Corporation, Lexington, MA (US)

(*) Notice: Subject to any disclaimer, the term of this patent is extended or adjusted under 35 U.S.C. 154(b) by 0 days.

(21) Appl. No.: 09/502,473

(22) Filed: Feb. 11, 2000

(51) Int. Cl.$^7$ ..................................................... H05G 1/02
(52) U.S. Cl. ........................... 378/198; 378/193; 378/197; 212/901
(58) Field of Search .................... 378/193, 197, 378/198; 212/901, 196

(56) References Cited

U.S. PATENT DOCUMENTS

| | | | | |
|---|---|---|---|---|
| 2,517,813 | * | 8/1950 | Wallace, Jr. ............................. | 212/35 |
| 2,917,189 | * | 12/1959 | Isaacs ..................................... | 212/66 |
| 3,367,512 | * | 2/1968 | Kaplan .................................... | 212/8 |
| 3,790,805 | * | 2/1974 | Foderaro ............................... | 250/522 |
| 4,989,229 | * | 1/1991 | Negrelli et al. ....................... | 378/198 |

* cited by examiner

Primary Examiner—David P. Porta
Assistant Examiner—Jurie Yun
(74) Attorney, Agent, or Firm—McDermott, Will & Emery

(57) ABSTRACT

A support system for a radiation treatment system includes a rotatable extension arm extending from a vertical shaft and a rotatable counterbalance extending diametrically opposed to the extension arm from the vertical shaft. The vertical shaft is rotatably supported by a support base. The support base may include a damping mechanism to damp the rotational motion of the vertical shaft relative to the support base, wherein the damping force is preferably proportional to the velocity of the vertical shaft. The radiation treatment system is suspended from a cable extending from a distal end of the extension arm. The extension arm can be formed from a first arm extending from the vertical shaft and a second arm rotatably coupled to the first arm in order to permit the radiation treatment system to be moved in horizontal direction. The cable supporting the radiation treatment system can be coupled to a vertical counterbalance weight to allow the vertical position of the radiation treatment system to be adjusted. In addition, mass of the vertical counterbalance weight can be adjusted to compensate for attachments which may be used with the radiation treatment system during treatment. The radiation treatment system can be supported to permit rotation about a horizontal axis that extends through the center of mass of the radiation treatment system. In addition position of the horizontal axis of rotation relative to the center of mass of the radiation treatment system can be adjusted to compensate for attachments which may change the center of mass of the radiation treatment system.

13 Claims, 10 Drawing Sheets

SUPPORT SYSTEM FOR A RADIATION TREATMENT APPARATUS

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to a miniaturized, programmable radiation source for use in delivering substantially constant or intermittent levels of x-rays to a specified region and, more particularly, to an apparatus for delivering a controlled dose of radiation to a localized volume of tissue, such as a volume of tissue of the human body.

In the field of medicine, radiation is used for diagnostic, therapeutic and palliative treatment of patients. The conventional medical radiation sources used for these treatments include large fixed position machines such as linear accelerators ("LINACs"), smaller transportable radiation delivery machines such as high-dose-rate after loaders, and catheters for low-dose-rate brachytherapy. The current state of the art treatment systems utilize computers to generate complex treatment plans for treating complex geometric volumes.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

Conventional radiation treatments systems, such as the LINAC used for medical treatment, utilize a high power remote radiation source and direct a beam of radiation at a target area, such as tumor inside the body of a patient. This type of treatment is referred to as teletherapy because the radiation source is located a predefined distance, approximately one meter, from the target. This treatment suffers from the disadvantage that tissue disposed between the radiation source and the target is exposed to radiation.

An alternative treatment system utilizing a point source of radiation is disclosed in U.S. Pat. Nos. 5,153,900 issued to Nomikos et al., 5,369,679 to Sliski et al., and 5,422,926 to Smith et al., all owned by the assignee of the present application, all of which are hereby incorporated by reference. The system includes a miniaturized, insertable probe capable of producing low power radiation in predefined dose geometries disposed about a predetermined location. This treatment is referred to as brachytherapy because the source is located close to or in some cases within the area receiving treatment. One advantage of brachytherapy is that the radiation is applied primarily to treat a predefined tissue volume, without significantly affecting the tissue in adjacent volumes.

Typical radiation therapy treatment involves positioning the insertable probe into or adjacent to the tumor or the site where the tumor or a portion of the tumor was removed to treat the tissue adjacent the site with a "local boost" of radiation. In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, it is desirable that the insertable probe be adjustably supported in a compliant manner to accurately position the radiation source with respect to the treated site and accommodate normal minor movements of the patient, such as movements associated with breathing.

In practice, the application of X-radiation to target tissue requires precise positioning of the X-ray source with respect to the target tissue, and maintaining that relative positioning throughout treatment. For therapeutic treatment of brain tumors using X-ray probes generally of the type disclosed in U.S. Pat. No. 5,153,900, stereotactic frames affixed to the patients skull are often used to effect the required relative positioning, as disclosed in U.S. Pat. No. 5,369,679. For treatment to other body parts, the user must otherwise support the relatively miniature X-ray probe. Such positioning using manual techniques has proven to be quite difficult.

Accordingly, it is an object of the present invention to provide an improved system for delivering radiation to a localized area. It is another object to provide an improved system for establishing and maintaining a desired position for therapeutic X-ray source.

SUMMARY OF THE INVENTION

The present invention is directed to a support system for a small, portable radiation source adapted for applying a dose of radiation to a volume of tissue such as a volume of tissue of the human body. In accordance with the present invention, the support system is adapted to support the small, portable radiation source in a substantially weightless state whereby the radiation source substantially maintains its horizontal and vertical position. The radiation source can be positioned by a physician for treatment and the radiation source will substantially maintain its horizontal and vertical position as well as its angular orientation about a first and second axis of rotation. In addition, the support system is adapted to permit minor movements of the area to be treated, such as to accommodate minor movements of a patient, for example, breathing.

The support system includes a support base, a rotatable, vertical shaft extending from the base along a first vertical axis. The support base may include a damping mechanism to damp the rotational motion of the vertical shaft relative to the support base, wherein the damping force is preferably proportional to the velocity of the vertical shaft. The support system further includes a horizontal extension coupled to the vertical shaft and a rotatable counterbalance coupled to the vertical shaft and extending in a diametrically opposite direction from the horizontal extension with respect to the first vertical axis. As the horizontal extension is rotated about the first vertical axis, the rotatable counterbalance remains diametrically opposite the horizontal extension to balance the support system. A portable radiation source can be coupled to a first end of a support cable which extends from the horizontal extension. Preferably, the horizontal extension is coupled to an upper portion of the vertical shaft and the rotatable counterbalance is coupled to a lower portion of the vertical shaft.

In one embodiment, the horizontal extension includes a first extension arm, coupled and extending from the vertical shaft and a second extension arm, rotatably coupled to the first extension arm by a rotatable coupling. The second extension arm is adapted to rotate about the second vertical axis with respect to the first extension arm.

In one embodiment, the vertical shaft includes a hollow portion and a vertical counterbalance weight, coupled to a second end of the support cable, which is suspended in the hollow portion. The weight of the vertical counterbalance weight can be adjusted to counterbalance the weight of the cable coupling and portable radiation source to permit the portable radiation source to be suspended in a substantially weightless configuration. Cable guides, such as pulleys, can be provided to guide the support cable along the first vertical axis into the first extension arm, along a second vertical axis through the rotatable coupling connecting the second extension arm to the first extension arm and through the second extension arm along the third vertical axis to the cable coupling and the portable radiation source. Thus, the vertical position of the portable radiation source can be easily adjusted and maintained while accommodating minor movements of the patient.

A cable coupling connects the cable to the portable radiation source and permits angular orientation of the portable radiation source to be adjusted relative to the cable coupling. Preferably, the support cable extends along a third vertical axis and the cable is connected to the cable coupling by a rotatable connection which permits the cable coupling and the portable radiation source to be freely rotated about the third vertical axis and accommodate minor movements of the patient.

The cable coupling can include a yoke which supports the portable radiation source and permits the portable radiation source to rotate about a horizontal axis. Preferably, the position of the horizontal axis with respect to the center of mass of the portable radiation source can be adjusted to accommodate the changes in the center of mass from various application adaptors which can be fitted to the probe of the portable radiation source. The portable radiation source can be positioned in a particular angular orientation about the horizontal axis and still accommodate minor movements of the patient.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1:
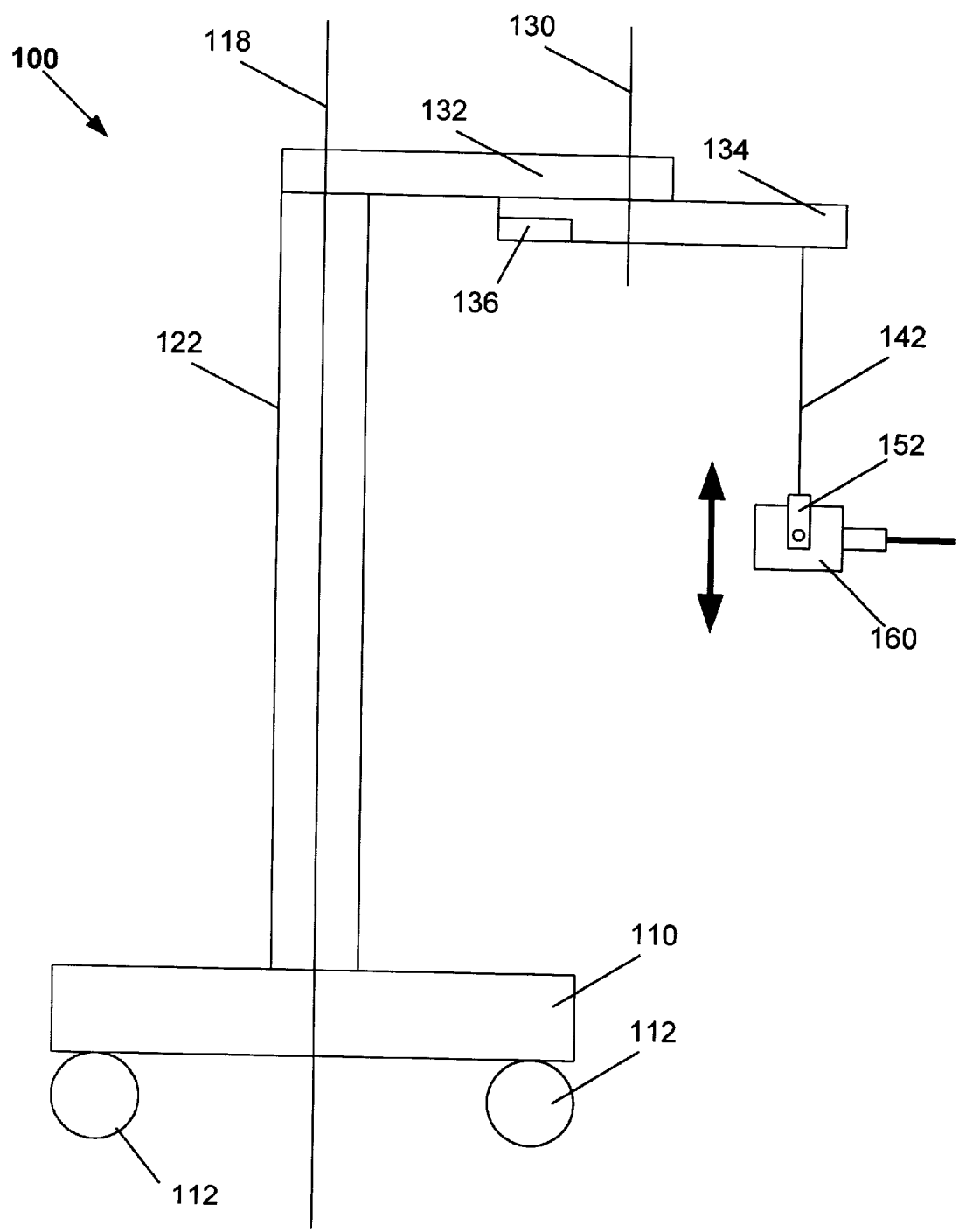
FIG. 1 is a diagrammatic side view of a support system for supporting a radiation treatment system in accordance with the present invention.
Figure 2:
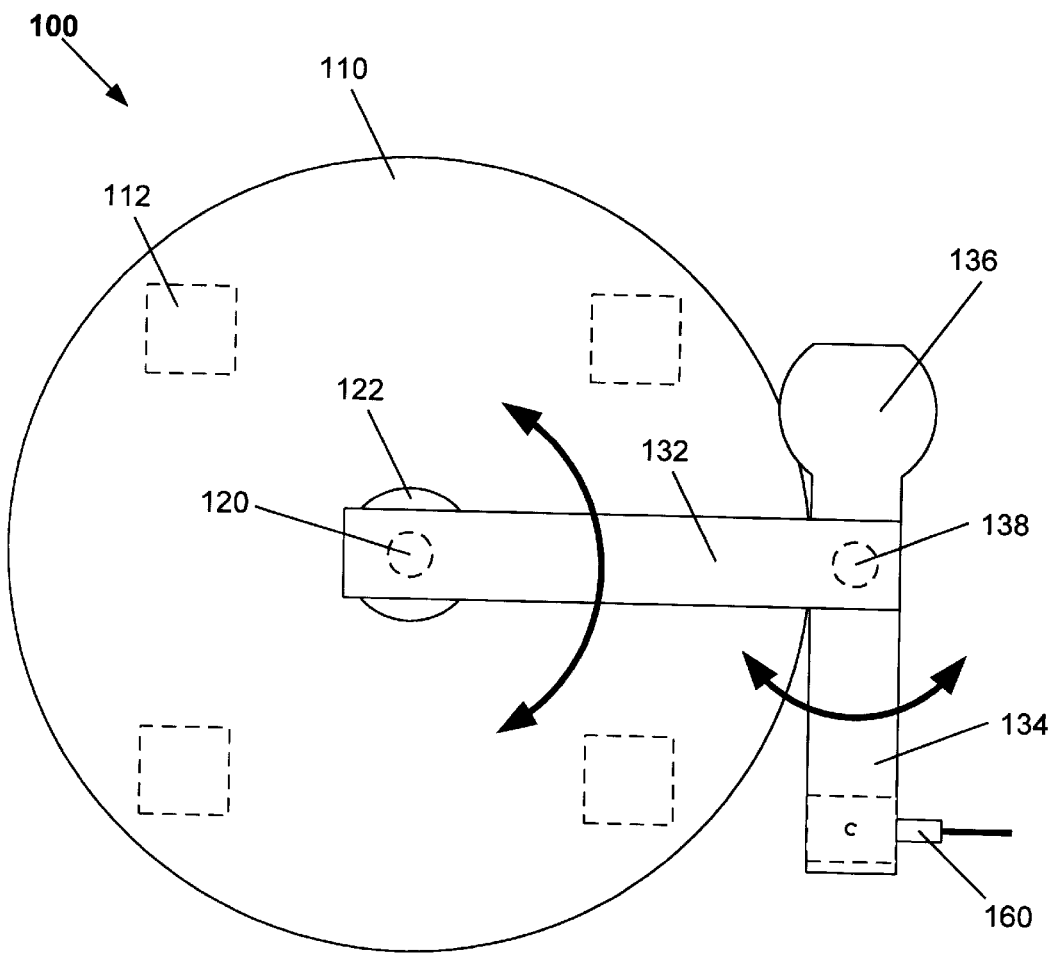
FIG. 2 is a diagrammatic top view of a support system for supporting a radiation treatment system in accordance with the present invention.

FIGS. 1 and 2 show two views of a support system 100 for a radiation treatment system 160 such as that disclosed in U.S. Pat. Nos. 5,153,900 and 5,369,494, which are hereby incorporated by reference. The radiation treatment system may include applicator systems (not shown) such as those disclosed in U.S. patent application Ser. Nos. 09/502,759, 09/502,273, and 09/505,413, which are hereby incorporated by reference.

The support system 100 includes a support base 110, a vertical shaft housing 122, a first extension arm 132 and a second extension arm 134. The support base 110 can include locking wheels 112 to permit the support system 100 to be transported and locked into position. The vertical shaft housing 122 extends vertically from the support base 110 along a first vertical axis 118. The first extension arm 132 is coupled to the upper end of a vertical shaft 120 (not shown in FIG. 1) and extends horizontally from the vertical shaft housing 122. The first extension arm 132 is adapted to rotate with the vertical shaft about the first vertical axis 118. The second extension arm 134 is rotatably coupled to the first extension arm 132 via rotatable coupling 138 (not shown in FIG. 1). The radiation treatment system 160 is suspended via a yoke 152 from a support cable 142 which extends from a first end of the second extension arm 134. Preferably, the other end of the second extension arm 134 includes a second extension arm counterbalance 136 selected and positioned to further counterbalance the weight of the radiation treatment system 160 supported by the first end of the second extension arm 134.

One end of the first extension arm 132 is mounted to the vertical shaft 120 and is adapted to rotate about the first vertical axis 118. The second extension arm 134 is mounted to the other end of the first extension arm 132 and adapted, via rotatable coupling 138 to rotate about a second vertical axis 130. When used in combination, the first extension arm and the second extension arm permit the radiation treatment system 160, which is suspended from the first end of the second extension arm 134, to be moved horizontally and positioned at virtually any location in a horizontal plane substantially perpendicular to the first vertical axis 118. The height of the radiation treatment system 160 (and horizontal plane) can be adjusted in order to accurately position the radiation treatment system 160 adjacent the area to be treated.

Figure 3:
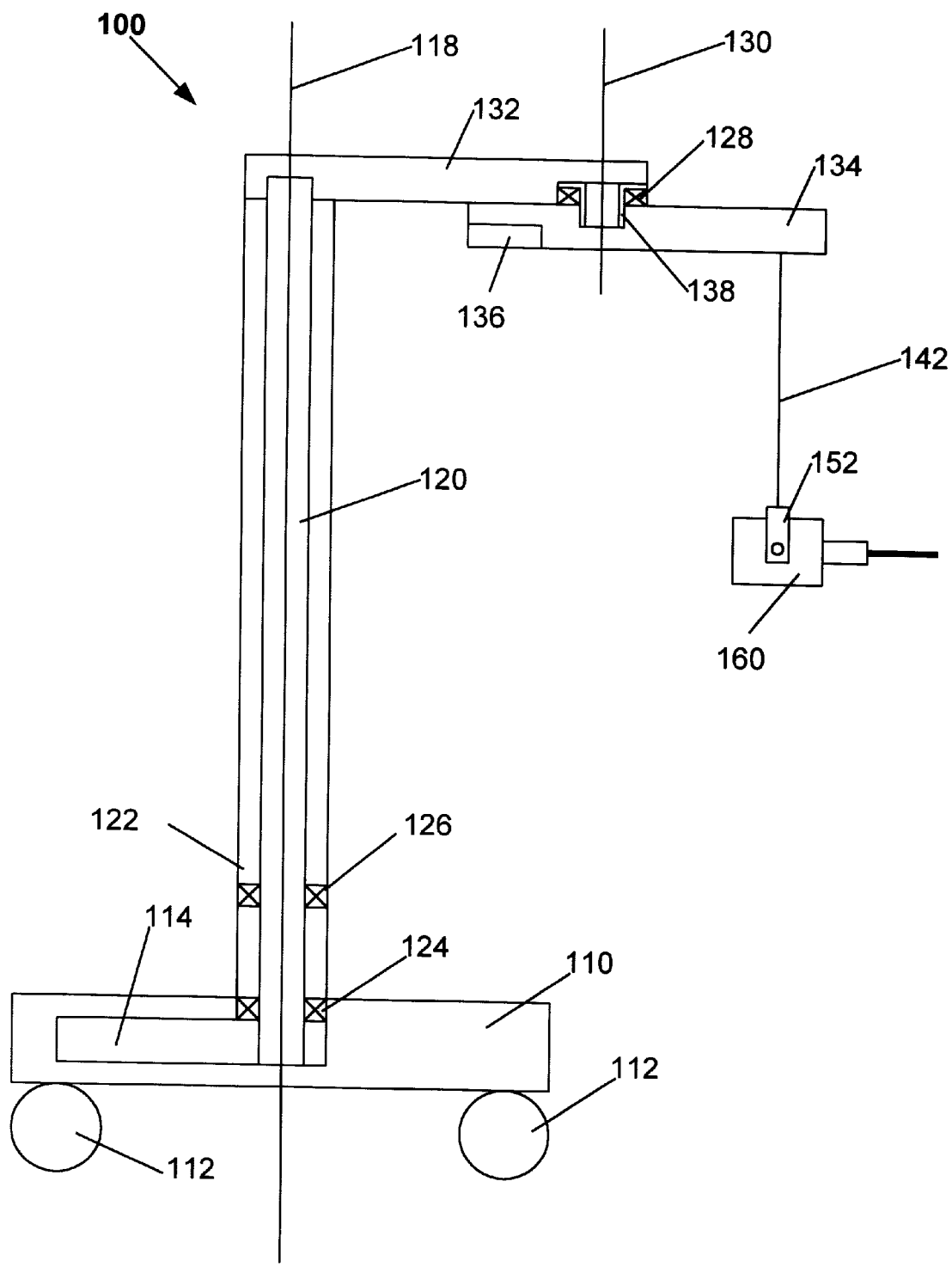
FIG. 3 is a diagrammatic side view showing a cross-section view of a support system for supporting a radiation treatment system in accordance with the present invention.
Figure 4A:
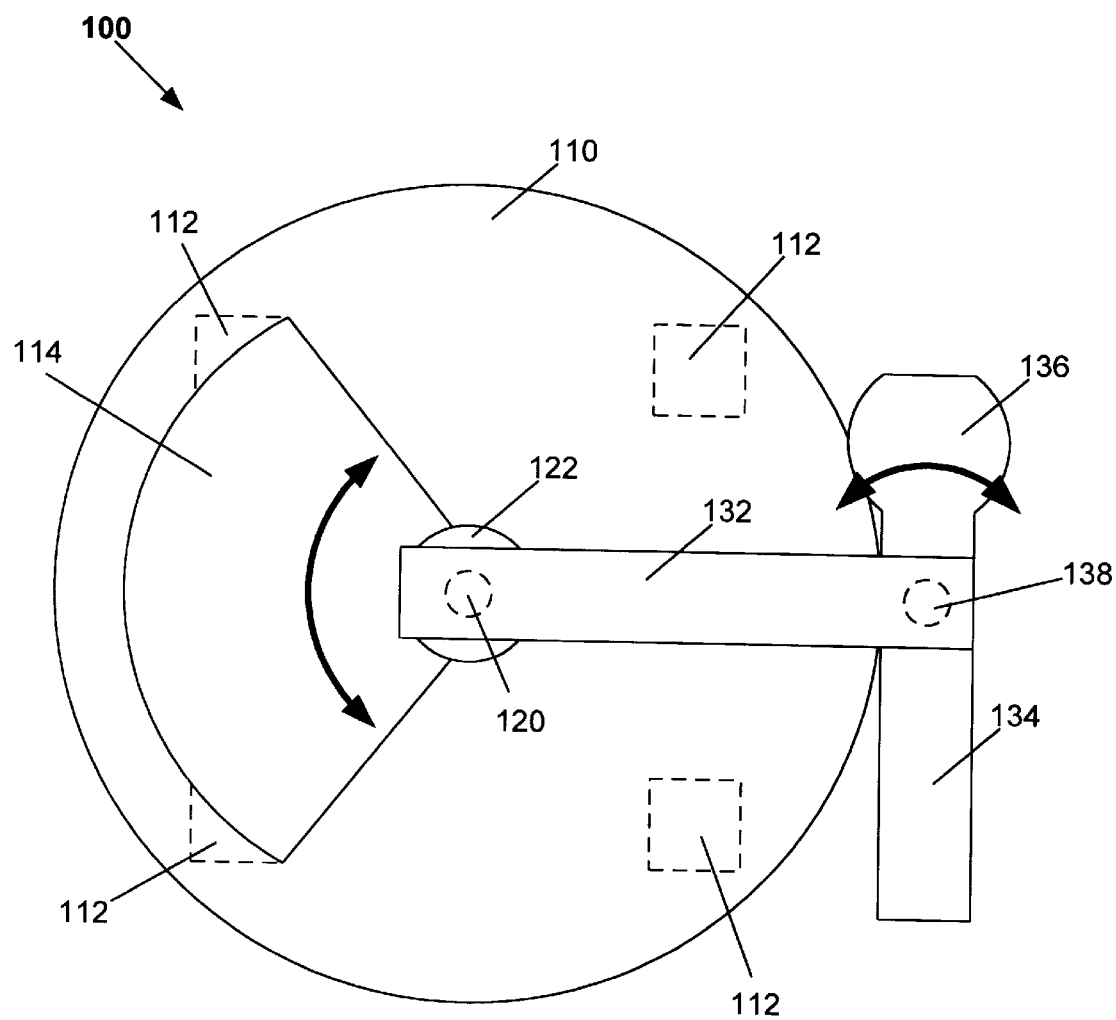
FIG. 4A is a diagrammatic top view showing a cross-section view of a support system for supporting a radiation treatment system in accordance with the present invention.

FIGS. 3 and 4A show section views of the support system 100 for supporting a radiation treatment system 160.

Preferably, inside the vertical housing 122 is a hollow vertical shaft 120 which is coupled to a rotatable counterbalance 114 at a bottom end and the first extension arm 132 at the top end. The rotatable counterbalance 114 extends in a diametrically opposite direction from the direction of extension of the first extension arm with respect to the first vertical axis. The rotatable counterbalance 114 serves to stabilize the support base 110 and the vertical shaft 120 of the support system 100 by counterbalancing the weight of the first extension arm 132, the second extension arm 134 and the radiation treatment system 160 with respect to the first vertical axis 118. Similarly, the second extension arm 134 includes a counterbalance 136 which serves to counterbalance the weight of the radiation treatment system 160 over the second extension arm 134 with respect to the second vertical axis 130. Preferably, the vertical shaft 120 is supported by bearings 124 and 126 in the support base 110 and the vertical shaft housing 122, respectively, to facilitate rotation. Similarly, the second extension arm 134 can be supported for rotation by rotatable coupling 138 by a bearing 128. In the preferred embodiment, the bearings 124, 126 and 128 can include precision rotary and/or thrust type ball bearings, but those skilled in the art will appreciate that other types of bearings or rotatable couplings would also suffice.

Figure 4B:
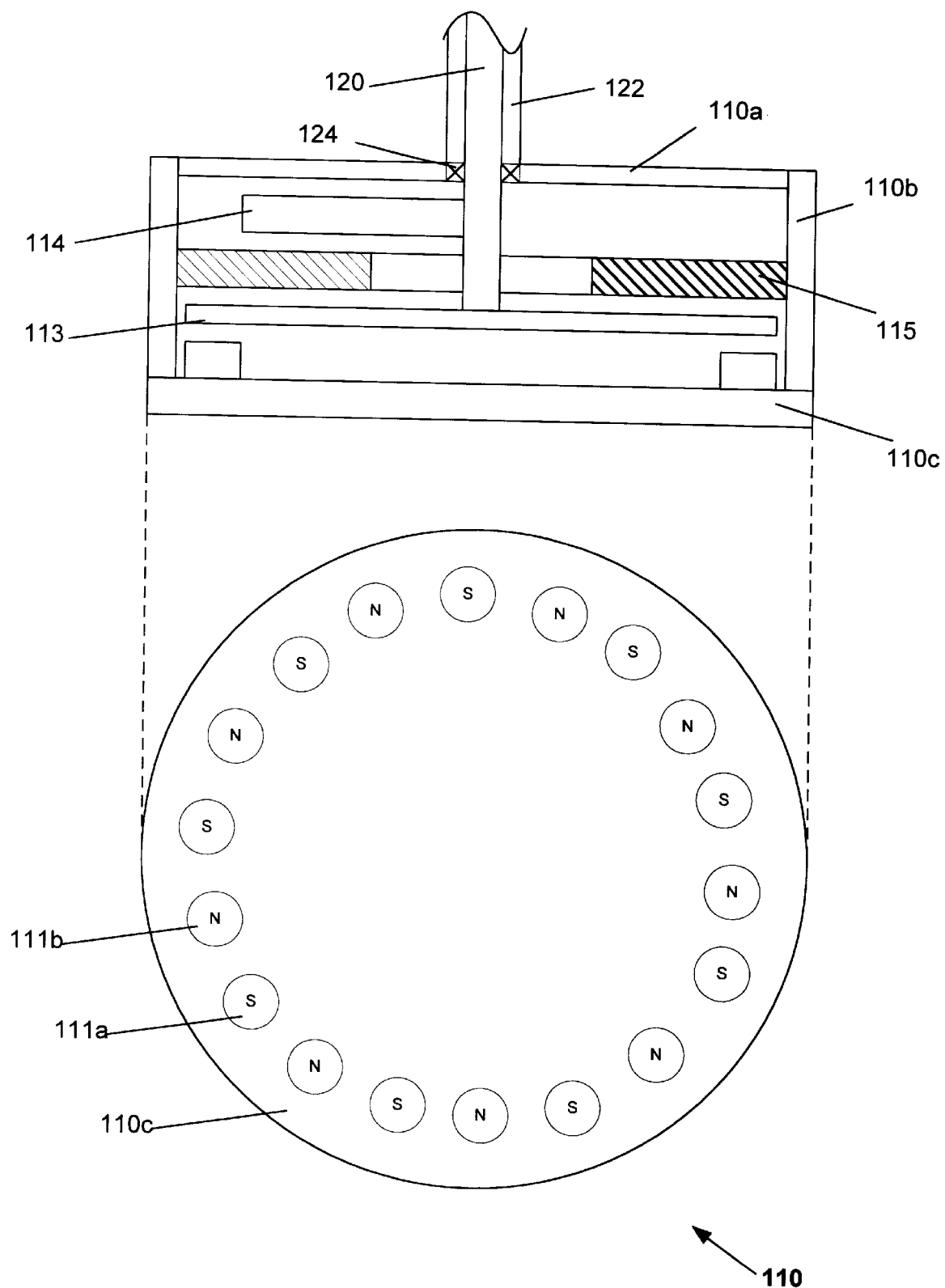
FIG. 4B is a diagrammatic cross sectional side view of the support base of FIG. 4A incorporating a damping mechanism, and including a top view of the bottom plate thereof.

As shown in FIG. 4B, in one embodiment of the support system 100, the support base 110 includes a damping mechanism. In such an embodiment, the damping mechanism damps the rotational motion of vertical shaft 120 relative to support base 110. Preferably, the amount of damping is proportional to the rotational velocity of vertical shaft 120. In the preferred form, support base 110 includes three segments which combine to substantially enclose the damping mechanism, which are: a ring shaped top plate 110a, a cylindrical housing 110b, and a disk shaped magnetically permeable bottom plate 110c. The damping mechanism includes a plurality of magnets 111a–b, a conductive disk shaped plate 113, and a less magnetically permeable ring 115, all oriented in substantially parallel planes. The magnets 111a (south polarity) and 111b (north polarity) are disposed in an alternate polarity circular arrangement about the perimeter of the bottom plate 110c and secured thereto (as shown from the top view of plate 110c). The conductive plate 113 is secured to the bottom of vertical shaft 120 and spans the diameter of the circular arrangement of magnets, and is positioned to be proximate thereto such that eddy currents are realized in plate 113 from magnets 111a and 111b. Ring 115 is then positioned above conductive plate 113 and substantially encloses said plate and magnet arrangement. As plate 113 and shaft 120 rotate, the electromagnetic interaction between plate 113 and magnets 111a and 111b causes a damping in the rotational motion of the plate, and thus shaft 120, in accordance with known principles. Effectively, such damping is similar to viscous damping, as will be appreciated by those skilled in the art. Preferably, plate 113 is comprised of aluminum and bottom plate 110c and ring 115 are comprised of steel.

Figure 5:
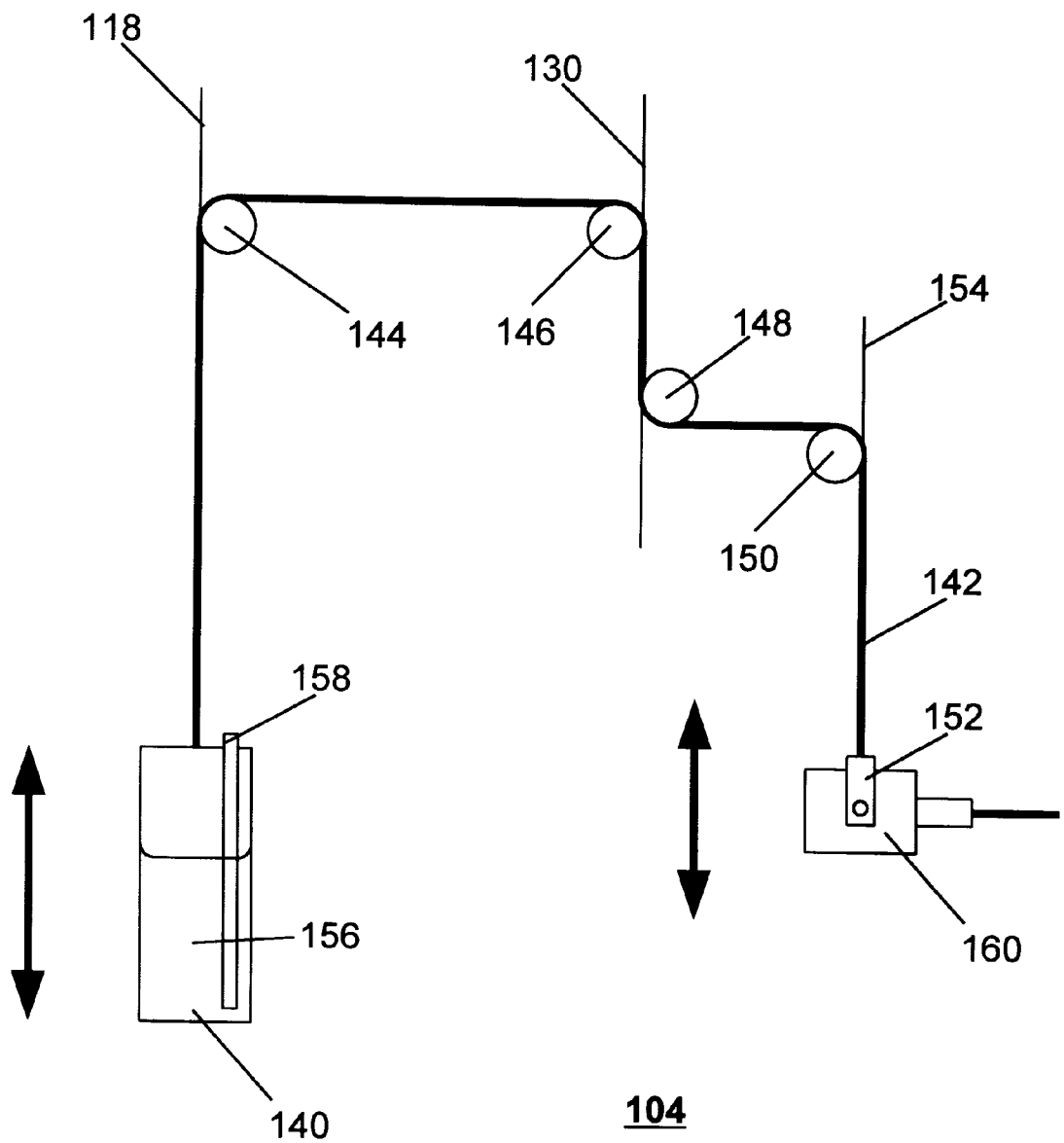
FIG. 5 is a diagrammatic side view showing a vertical support subsystem for a system for supporting a radiation treatment system in accordance with the present invention.

FIG. 5 shows a schematic view of a vertical counterbalance system 104 which permits the radiation treatment system to be positioned in virtually any location along a third vertical axis 154. The vertical counterbalance system 104 includes a cable coupling or yoke 152 which supports the radiation treatment system 160, a support cable 142 which engages pulleys 144, 146, 148 and 150 and a vertical counterbalance weight 140. Preferably, the weight of the counterbalance weight 140 can be adjusted to be substantially the same as the yoke 152 and the radiation treatment system 160 whereby when the counterbalance weight 140 and the radiation treatment system 160 and yoke 152 are connected to opposite ends of the support cable 142, the radiation treatment system can be suspended in a substantially weightless configuration. The radiation treatment system 160 can be raised or lowered along the third vertical axis 154 by the application of a minimum of force and the radiation treatment system 160 will maintain its position along the third vertical axis 154.

In the preferred embodiment, the vertical counterbalance weight 140 includes a hollow chamber 156 and an access tube 158 which permits a fluid such as water or oil to be added or removed from the hollow chamber 156. A simple hypodermic syringe or similar device can be used to add fluid to or remove fluid from the chamber to precisely adjust the weight of the vertical counterbalance weight 140 to be substantially equal to the weight of the yoke 152 and radiation treatment system 160. The weight of the vertical counterbalance weight 140 can also be changed to compensate for the weight of attachments, for example the applicator adapters disclosed in U.S. patent application Ser. Nos. 09/502,759, 09/502,273, and 09/505,413, to be mounted to the radiation treatment system 160.

Figure 6:
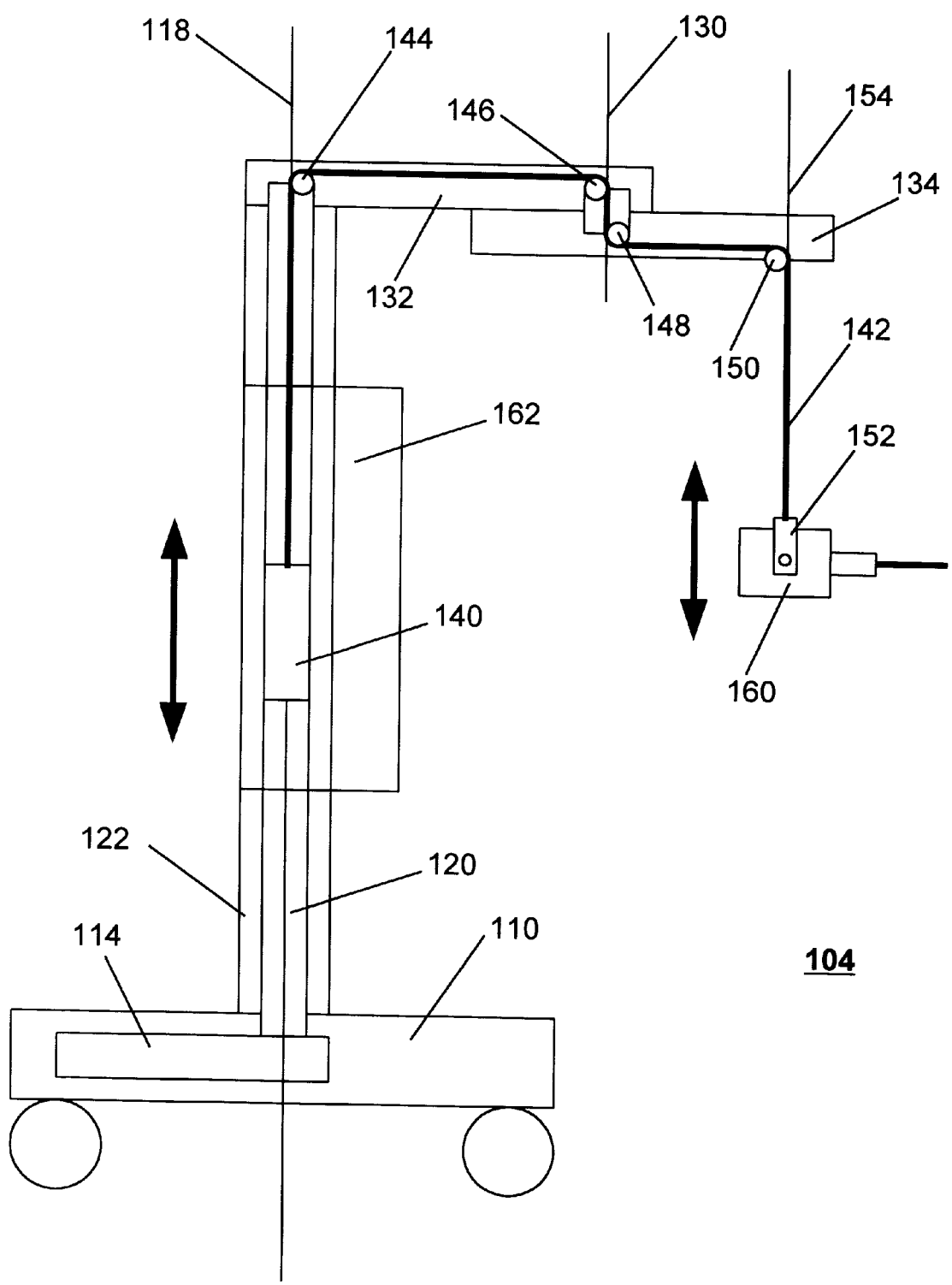
FIG. 6 is a diagrammatic side view showing a vertical support subsystem in a support system for supporting a radiation treatment system in accordance with the present invention.
Figure 7:
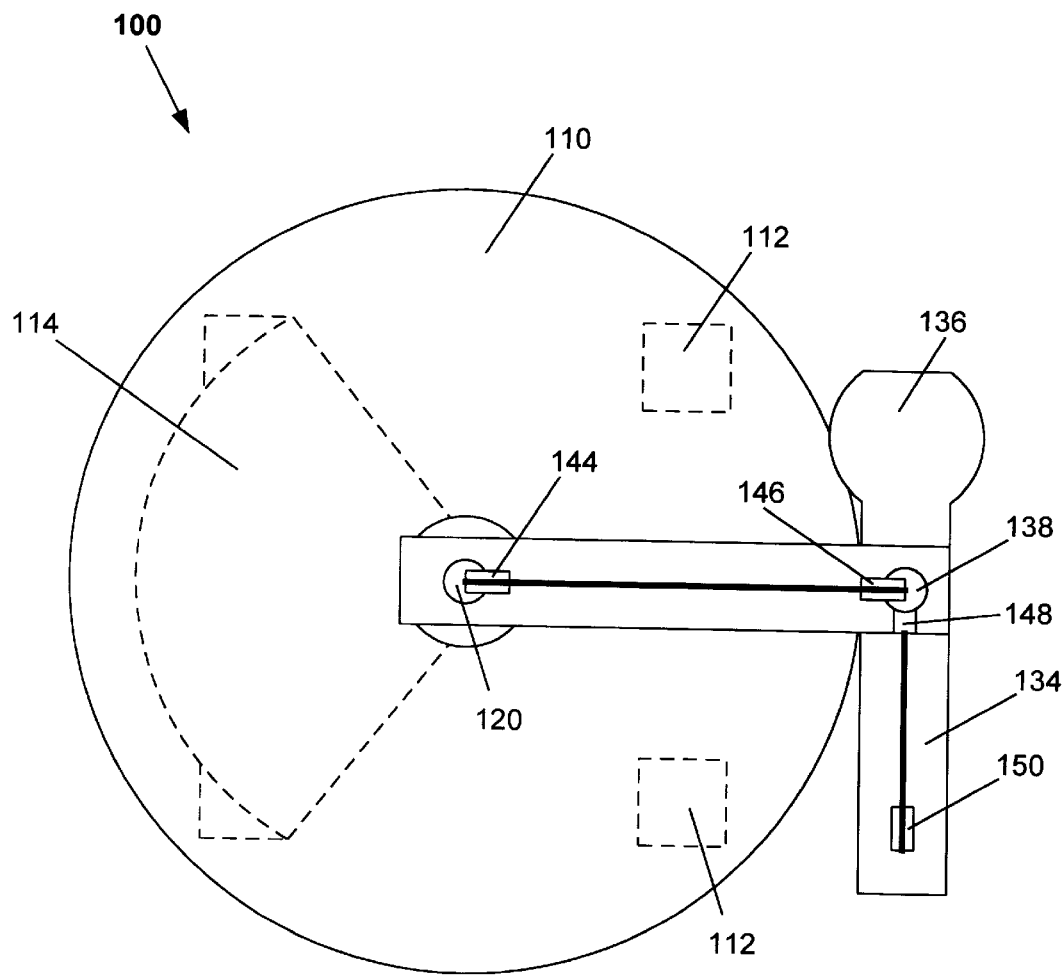
FIG. 7 is a diagrammatic top view showing a vertical support subsystem in a support system for supporting a radiation treatment system in accordance with the present invention.

FIGS. 6 and 7 show a diagrammatic view of the vertical counterbalance system 104 incorporated in the support system 100 of the present invention. The vertical counterbalance 140 is coupled to one end of the support cable 142 and is suspended within a hollow portion of the vertical shaft 120. The support cable 142 extends vertically along the first vertical axis 118 to the first pulley 144. From the first pulley 144, the support cable 142 extends, within the first extension arm 132, to the second pulley 146. From the second pulley 146, the support cable 142 extends vertically along the second vertical axis 130 to the third pulley 148. From the third pulley 148, the support cable 142 extends within the second extension arm 134 to the fourth pulley 150. From the fourth pulley 150, the support cable 142 extends vertically along the third vertical axis 154 to the yoke 152 which supports the radiation treatment system 160.

Preferably, the pulleys 144, 146, 148, 150 and support cable 142 are arranged and aligned within the structure of the vertical shaft 120, the first extension arm 132 and the second extension arm 134 to permit the first extension arm 132 and the second extension arm 134 to rotate about the first vertical axis 118 and second vertical axis 130, respectively, without interfering with the operation of the vertical counterbalance system 104. The first pulley 144 is coupled to the first extension arm 132 and adapted to rotate about the first vertical axis 118 with the first extension arm 132. Preferably, the first pulley 144 is configured and aligned to guide the support cable 142 along the first vertical axis 118 in order to permit the counterbalance weight 140 to move vertically along the first vertical axis 118 regardless of the angular orientation of the first extension arm 132 with respect to the first vertical axis 118. The second pulley 146 and third pulley 148 are coupled to the first extension arm 132 and second extension arm 134, respectively and are adapted to rotate with respect to each other about the second vertical axis 130. Preferably, the second pulley 146 and the third pulley 148 are configured and aligned to guide the support cable 142 along the second vertical axis 130 in order to permit the support cable 142 to move vertically along the second vertical axis 130 regardless of the angular orientation of the second extension arm 134 with respect to the first vertical arm 132 about the second vertical axis 130.

Figure 8:
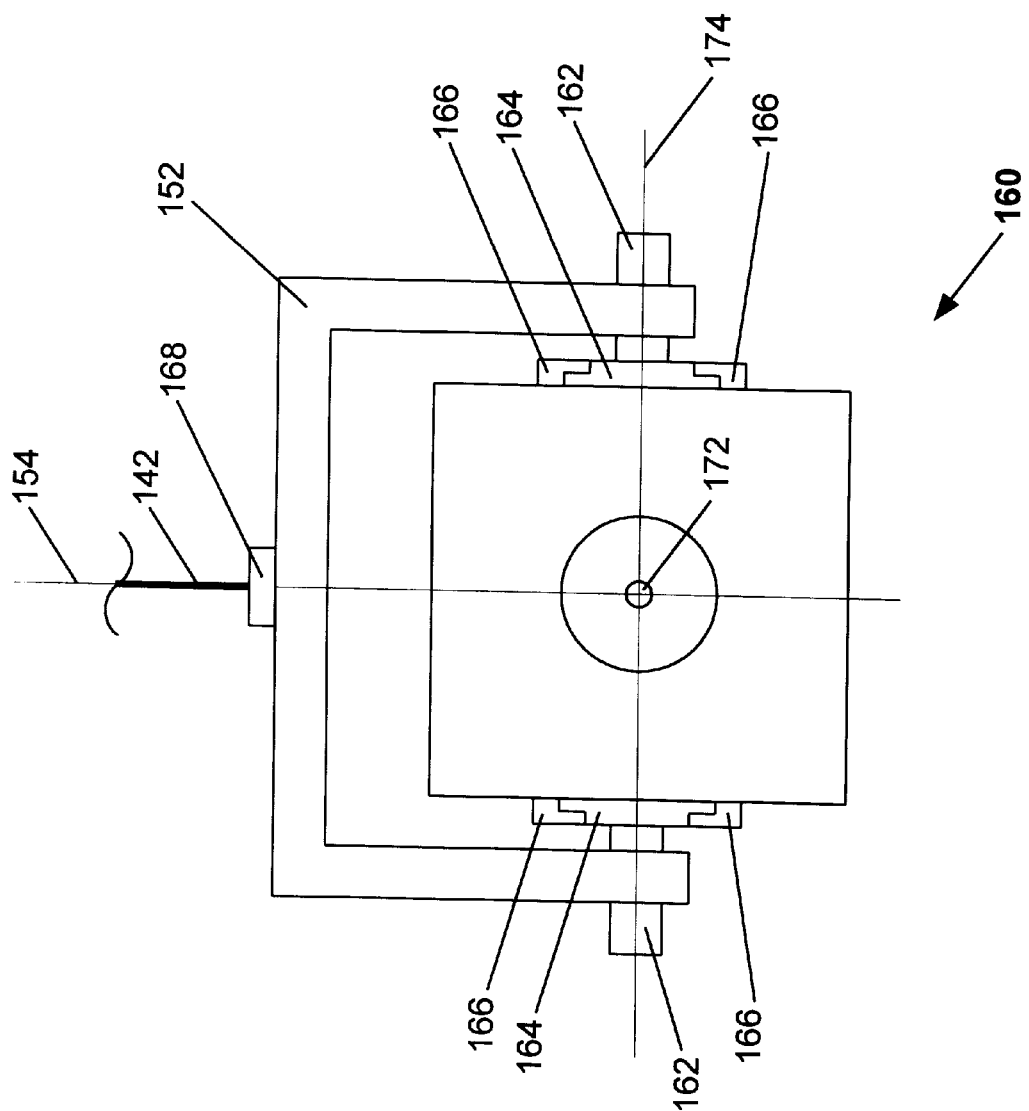
FIG. 8 is a diagrammatic front view of the portable radiation source and the cable coupling in accordance with the present invention.
Figure 9:
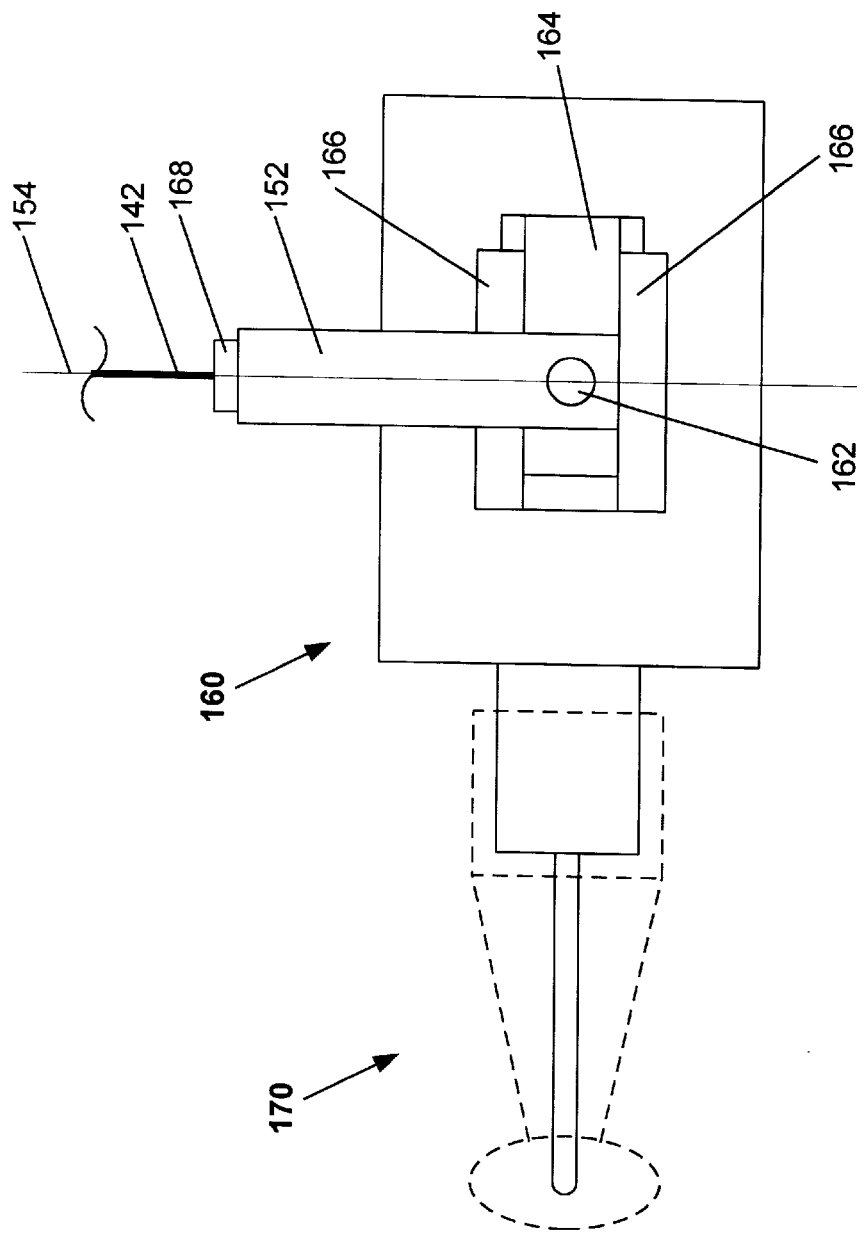
FIG. 9 is a diagrammatic side view of the portable radiation source and the cable coupling in accordance with the present invention.

As shown in FIGS. 8 and 9, the yoke 152 is preferably adapted to support the radiation treatment system 160 along the third vertical axis 154 and a horizontal axis 174 that both extend through the center of mass 172 of the radiation treatment system 160 in order to permit the radiation treatment system to be oriented with respect to the third vertical axis 154 and the horizontal axis 174. This permits the radiation treatment system 160 to be balanced about the vertical 154 and horizontal 174 axes and to remain in a set position after it has been moved into position adjacent the area to be treated. Preferably, the support cable 142 is connected to the yoke 152 via a substantially frictionless connection 168 that allows the yoke 152 and the radiation treatment system 160 to be freely rotated about the third vertical axis 154. Preferably, the yoke 152 supports the radiation treatment system 160 via pins or shafts 162 which fit into bearings (not shown) mounted in the yoke 152. As shown in FIGS. 8 and 9, the shaft 162 is coupled to a slide plate 164 which mates with brackets 166 to permit the position of the shaft 162 and the axis of rotation 174 to be adjusted relative to the center of mass of the radiation treatment system 160 to accommodate attachments 170 that could change the position of the center of mass of the radiation treatment system 160. A set screw or similar fastener (not shown) could be use to lock the slide plate 164 into place. Alternatively, a threaded shaft could be used to move the slide plate relative to brackets 166 in order to change the position of the horizontal axis of rotation relative to the center of mass of the radiation treatment system 160. Instead of a shaft 162 and bearing arrangement, any means for permitting rotation of the radiation treatment system about the horizontal axis 174, such a ball and socket or a rotatable point and cup joint, could be used.

In the preferred embodiment, the rotatable counterbalance 114 is constructed of lead or cast iron and formed in the shape of a wedge. Preferably, the weight and weight distribution with respect to the first vertical axis 118 of the rotatable counterbalance 114 are selected to counterbalance the moment of the first extension arm 132, the second extension arm 134 and the radiation treatment system 160. The vertical shaft 120 preferably includes a substantially hollow tube to permit the vertical counterbalance weight 140 to move within it. Preferably, the vertical shaft 120 also includes a removable portion or access door 162 which provides access to the vertical counterbalance weight 140 suspended within it.

During treatment, the radiation treatment system 160 with an attached applicator adapter 170 is supported by the support system 100. Preferably, bearings provide substantially effortless movement of the radiation treatment system 160 into position for treatment. This allows the physician applying treatment to guide the tip of the applicator without having to support the weight of the device for the duration of the treatment. In addition, the applicator can remain in position during treatment, which can last on the order of up to several hours, and accommodate minor movements of the patient or treatment site, such as the movements associated with breathing.

The invention may be embodied in other specific forms without departing from the spirit or essential characteristics thereof. For example, various pulley and counter balance arrangements may be used, as well as various moveable arm arrangements for supporting the radiation treatment system. In other embodiments, rather than purely mechanical means for positioning and supporting the radiation treatment system, electromechanical and hydraulic means could also be used to varying degrees. The present embodiments are therefore to be considered in all respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A support system for a portable radiation source comprising:

A. a support base,
   B. a vertical shaft extending from a first end at the support base, along a first vertical axis to a second end distal from the support base, said vertical shaft being adapted to rotate about said vertical axis with respect to the support base,
   C. a horizontal extension rotatably coupled about the vertical axis to and extending horizontally from the vertical shaft at or near the second end,
   D. a first counterbalance rotatably coupled about the vertical axis to said vertical shaft and extending in a diametrically opposite direction from said extension with respect to said first vertical axis,
   E. a support cable having a first end extending from said extension and said cable extending along said vertical shaft,
   F. a cable coupling affixed to the support cable adapted for coupling the first end of the support cable to the portable radiation source, and
   G. a vertical counterbalance having a hollow portion coupled to the second end of said support cable.

2. A support system according to claim 1 wherein said vertical shaft includes a substantially hollow portion and said second end of said cable and said counterbalance are disposed with said hollow portion said support system further comprises:

a vertical counterbalance coupled to the second end of said support cable.

3. A support system according to claim 2 wherein said support cable extends from said cable coupling through at least a portion of said horizontal extension to said vertical counterbalance and wherein said support system further includes a first cable guide adapted for guiding the support cable from said cable coupling through said horizontal extension and a second cable guide adapted for guiding the support cable from said horizontal extension to said vertical counterbalance in said hollow portion of the vertical shaft.

4. A support system according to claim 3 wherein at least one of said first cable guide and said second cable guide includes a pulley.

5. A support system according to claim 1 wherein said horizontal extension comprises a first extension arm coupled to and extending from the vertical shaft to a distal end,
   a second extension arm pivotally coupled to said first extension arm at said distal end by a pivotal coupling, said second extension arm being adapted at said pivotal coupling to rotate about a second vertical axis with respect to said first extension arm, and
   wherein said first end of said support cable extends from second extension arm.

6. A support system according to claim 5 wherein said vertical shaft includes a substantially hollow portion and said support system further comprises:

a vertical counterbalance disposed with said hollow portion and coupled to the second end of said support cable.

7. A support system according to claim 6 wherein said support cable extends from said cable coupling through at least a portion of said first extension arm and at least a portion of said second extension arm to said vertical counterbalance and wherein said support system further includes a first cable guide adapted for guiding the support cable from said cable coupling through said first extension arm, a second cable adapted for guiding the support cable from said first extension arm to said second extension arm and a third cable guide adapted for guiding the support cable from said second extension arm to said vertical counterbalance in said hollow portion of the vertical shaft.

8. A support system according to claim 7 wherein at least one of said first cable guide, said second cable guide and said third cable guide includes a pulley.

9. A support system according to claim 1 where said cable coupling is adapted to couple a first end of the support cable to said portable radiation source, and adapted to permit said portable radiation source to rotate about a first horizontal axis and third vertical axis.

10. A support system according to claim 2 wherein said cable coupling is adapted for adjusting the position of the first horizontal axis relative to a center of mass of said portable radiation source.

11. A support system according to claim 1, further comprising a damping mechanism that damps the rotation of the vertical shaft with respect to the support base.

12. A support system according to claim 11, wherein the damping mechanism is an electromagnetic damping mechanism.

13. A support system according to claim 12 wherein the support base includes a bottom plate substantially orthogonal to said first vertical axis and wherein the electromagnetic damping mechanism includes:

a plurality of magnets coupled to said bottom plate and disposed in an alternating polarity and substantially circular arrangement about said first vertical axis at a radius of r1; and a circular conductor secured to a bottom end of said vertical shaft and rotatable in a plane that is parallel to said circular arrangement of magnets, wherein said conductor has a radius of at least about r1 about said first vertical axis and wherein said conductor is sufficiently proximate to said magnets to cause eddy currents to be generated in said conductor.

* * * * *